United States Patent [19]

Mimoun et al.

[11] 4,085,145

[45] Apr. 18, 1978

[54] PROCESS FOR MANUFACTURING CARBONYL COMPOUNDS BY OXIDATION WITH MOLECULAR OXYGEN OF OLEFINIC COMPOUNDS IN LIQUID PHASE IN THE PRESENCE OF SOLUBLE BIMETALLIC CATALYSTS

[75] Inventors: Hubert Mimoun, Rueil Malmaison; Do Thao, Le Pecq; Irénée Seree de Rochi, Rueil Malmaison, all of France

[73] Assignee: Institut Francais du Petrole, Rueil-Malmaison, France

[21] Appl. No.: 686,245

[22] Filed: May 13, 1976

[30] Foreign Application Priority Data

May 13, 1975    France .................................. 75 15110

[51] Int. Cl.$^2$ .............................................. C07C 45/10
[52] U.S. Cl. ................................ 260/592; 260/597 B; 260/591; 260/590 R
[58] Field of Search .................... 260/592, 597 B, 591, 260/590 B

[56] References Cited

U.S. PATENT DOCUMENTS

| | | | |
|---|---|---|---|
| 3,154,586 | 10/1964 | Bander et al. | 260/597 B |
| 3,346,624 | 10/1967 | Schaeffer et al. | 260/597 B |
| 3,365,499 | 1/1968 | Clement et al. | 260/597 B |
| 3,927,111 | 12/1975 | Robinson | 260/597 B |
| 3,932,521 | 1/1976 | Gloyer et al. | 260/597 B |

FOREIGN PATENT DOCUMENTS

| | | | |
|---|---|---|---|
| 2,234,249 | 1/1973 | Germany | 260/597 B |
| 2,205,899 | 8/1972 | Germany | 260/597 B |

*Primary Examiner*—James O. Thomas, Jr.
*Assistant Examiner*—James H. Reamer
*Attorney, Agent, or Firm*—Millen & White

[57] ABSTRACT

Carbonyl compounds are manufactured by oxidation of olefines with molecular oxygen in the presence of a catalytic system comprising both a specific rhodium compound and a specific compound of a metal selected from iron, cobalt, nickel and copper. The reaction is conducted in a substantially anhydrous organic solvent selected from alcohols, polyols and glycol monoethers.

10 Claims, No Drawings

PROCESS FOR MANUFACTURING CARBONYL COMPOUNDS BY OXIDATION WITH MOLECULAR OXYGEN OF OLEFINIC COMPOUNDS IN LIQUID PHASE IN THE PRESENCE OF SOLUBLE BIMETALLIC CATALYSTS

The present invention concerns a process for manufacturing carbonyl compounds, particularly methyl ketones, in the liquid phase, by the catalytic oxidation of olefins with molecular oxygen, in a substantially anhydrous medium and in the presence of soluble bimetallic catalysts.

In the processes of the Wacker type for converting olefins to ketones (U.S. Pat. No. 3,080,425), the catalysts are, for example, palladium chloride or rhodium oxyhydrate associated with copper chloride or iron sulfate; these processes are operated in the aqueous phase and water is the oxidizing agent for the reaction.

According to the French Pat. No. 1,210,009, rhodium, iridium or palladium chloride associated with copper chloride is also used as catalyst for oxidizing olefins in the aqueous phase, and water is the oxidizing agent.

According to the two above patents, it is essential to operate in a strongly acidic medium (concentrated acids are employed).

Other patents also utilize the presence of water to carry out reactions of the same kind in an organic solvent with palladium catalysts of the same type: French Pat. Nos. 1,564,635 and 1,395,129; U.S. Pat. No. 3,370,073.

The process according to the invention is performed essentially in the liquid phase, in a water-free solvent, in the presence of a rhodium catalyst, the other noble metals of the VIIIth group being excluded. Thus, by using rhodium instead of palladium, a metal commonly used in liquid phase, processes far higher selectivities are obtained, particularly when converting terminal olefins to methylketones, as well as far higher reaction rates.

According to the process of the invention, the catalyst comprises both at least one organometallic salt or complex [A] and at least one organometallic salt or compound [B], of the general formulas:

[A] : $M_1 X_n L_m$

[B] : $M_2 Z_p L_q$

In the salt of complex [A], $M_1$ is rhodium.

X is an anionic group, preferably halogen (usually chlorine of fluorine), a carboxylate, a sulfate, a nitrate, a perchlorate, a thiocyanate, a tetrafluoroborate, an acetyl acetonate or a cyclopentadienyl.

n is a integer selected from 1, 2 and 3.

L is a coordinate, preferably a water molecule or an organic compound selected preferably from the olefins, diolefins, phosphines, dimethylsulfoxide and an acetylacetonate group.

m is an integer from 1 to 3.

Non-limitative examples of rhodium complexes are:
rhodium fluoride, $RhF_3, 3H_2O$
rhodium chloride, $RhCl_3, 3H_2O$
rhodium bromide, $RhBr_3, 2H_2O$

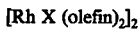 [Rh X (olefin)$_2$]$_2$ where X is chlorine or bromine and olefin is ethylene, propylene, tetrafluorethylene or cyclooctene; for example [RhCl (C$_2$H$_4$)$_2$]$_2$ where C$_2$H$_4$ is ethylene.

 [Rh X (polyolefin)]$_2$ where X is chlorine or bromine, and polyolefin is 1,5-cyclooctadiene, 1,5-hexadiene, butadiene or cyclododecatriene, for example [RhCl (C$_8$H$_{12}$)]$_2$ where C$_8$H$_{12}$ is 1,5-cyclooctadiene.

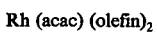 Rh (acac) (olefin)$_2$ where "acac" is an acetylacetonate group and olefin is ethylene or tetrafluorethylene.

In the salt or complex [B] to be used with the complex A:

$M_2$ is a transition metal selected from iron, cobalt, nickel and copper,

Z is an anionic group, preferably halogen, a carboxylate, a sulfate, a nitrate, a perchlorate or a tetrafluoroborate.

p is an integer selected from 1, 2 and 3.

L' is a coordinate, preferably a molecule of water or an organic molecule, for example dimethylformamide, hexamethylphosphoramide or dimethylsulfoxide.

q is 0 or an integer from 1 to 6.

Non-limitative examples are:
iron, cobalt, nickel and copper perchlorates and nitrates of the general formulas $M_2(ClO_4)_2, 6H_2O$ and $M_2(NO_3)_2, 6H_2O$.

copper and iron halides of the formula $M_2Z_p, qH_2O$ with Z = fluorine, chlorine or bromine and $M_2$ = iron or copper, p is 2 or 3 and q is 0 or an integer from 1 to 6.

complexes such as: Cu (ClO$_4$)$_2$, 4 L'; Fe (ClO$_4$)$_2$, 4 L' or Cu (NO$_3$)$_2$, 4 L', where L' is a coordinate such as dimethylformamide, hexamethylphosphoramide or dimethylsulfoxide; for example:

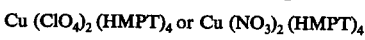 Cu (ClO$_4$)$_2$ (HMPT)$_4$ or Cu (NO$_3$)$_2$ (HMPT)$_4$ where HMPT is hexamethylphosphoramide.

This invention applies to branched or unbranched olefinic compounds having from 2 to 16 carbon atoms per molecule and whose general formula is $R_1$— CH = CH — $R_2$ where $R_1$ and $R_2$ are identical or not and represent either hydrogen atoms or alkyl, aryl, alkylaryl or aralkyl radicals having 1 - 14 carbon atoms per molecule.

According to the invention, there are preferably used primary terminal olefins of the above general formula where $R_1$ = H and $R_2$ = alkyl, aryl, alkylaryl or aralkyl; they contain 3 - 16 carbon atoms and yield methylketones selectively. They are thus of the formula $CH_2$ = CH — $R_2$. From ethylene, there is obtained ethanal.

Non-limitative examples are ethylene, propylene, 1-butene, 1-pentene, 1-hexene, 1-heptene, 1-octene, 1-nonene, 1-decene, 1-dodecene, 4-methyl-1-pentene, 3,3-dimethyl-1-butene, 5-methyl-1-hexene and styrene.

The primary terminal olefins may be used in a pure state or diluted with other inert or olefinic hydrocarbons. Thus oxidizing partially hydrogenated steam cracking C$_4$ cuts containing a mixture of olefins such as 1-butene and cis and trans 2-butenes and butane leads selectively to the formation of methylethyl ketone obtained by oxidation of 1-butene, the other olefins being only slightly oxidized.

The oxidation reaction is conducted in liquid phase in an organic solvent; the catalyst in the form of its two constituents [A] and [B] being solubilized in the medium.

The solvent is an alcohol or a polyalcohol. It comprises preferably from 1 to 20 carbon atoms per molecule. The alcohol may be a primary, secondary or tertiary alcohol; the polyalcohol (or polyol) comprises at least 2 alcohol groups.

Examples of solvents are: methanol, ethanol, n-propanol, isopropanol, 2-butanol, 3,3-dimethyl-2-butanol, cyclohexanol, methyl phenyl carbinol, ethylene glycol, 1,2-propane diol and glycerol.

Other useful solvents are the glycol monoethers (cellosolves) of the formula $R - O - CH_2 - CH_2OH$, particularly methylcellosolve of the formula $CH_3 - O - CH_2 - CH_2OH$.

The alcoholic or polyalcoholic solvents yield better results than those obtained with other conventional solvents such as ketones, ethers and esters.

It is essential that the solvent be substantially anhydrous since, irrespective of the solvent, the reaction improves when the water concentration in the medium decreases. Water may be tolerated, however, at concentrations up to 1% b.w. in the solvent, and preferably not above 0.5%, whenever possible not above 0.2%. A dehydration agent may be added to the medium, if necessary, for example 2,2'-dimethoxypropane.

The temperature at which the reaction takes place is from about 0° C to about 150° C, preferably from 30° C to 130° C.

The oxidation gas may be pure oxygen or oxygen diluted with nitrogen or any inert gas.

The oxygen partial pressure is from 0.1 to 25 bars.

Conversely to the prior art processes, it is conducted in substantially neutral medium (pH usually between about 6 and 8).

In the process according to the invention, the molar ratio [B]/[A] is usefully from 0.5 to 10 and preferably from 1 to 4.

The molar ratio [A]/olefine, in mole per liter, is usefully from $10^{-3}$ to $5 \times 10^{-1}$, preferably from $5 \times 10^{-3}$ to $10^{-1}$.

The present invention is illustrated by the following examples:

EXAMPLE 1

A heat-insulated glass reactor is charged with 70 cc anhydrous isopropyl alcohol, 30 cc of 1-hexene (0.236 mole), and then 2 millimoles of hydrated rhodium chloride and 4 millimoles of copper perchlorate $Cu(ClO_4)_2$, $6H_2O$. The pH of the solution is about 7. The temperature of the reactor is raised to 40° C. The free space of the reactor is then fed with pure oxygen up to a total pressure of 1.2 bars. A magnetic stirrer is started to stir the contents of the reactor. The oxygen pressure decreases in the reactor and is maintained constant by permanent supply of pure oxygen. After 4 hours of reaction, 0.05 mole of oxygen has been absorbed, 0.099 mole of 2-hexanone has been formed and 0.109 mole of 1-hexene consumed (molar selectivity: 91%).

EXAMPLE 1 - A (for comparison)

Example 1 is repeated, except that 70 cc of water is used, instead of 70 cc of isopropyl alcohol. After 4 hours, no substantial absorption of oxygen has been observed. The pH of the solution then decreased to 1 by addition of concentrated hydrochloric acid; stirring is continued for 4 hours and there is now observed an absorption of 0.02 mole oxygen. 0.025 mole of 2-hexanone is formed and 0.044 mole 1-hexene is consumed (molar selectivity: 57%).

EXAMPLE 1 - B

Example 1 is repeated, except that a mixture of 68 cc of isopropyl alcohol and 2 cc of water has been used, instead of 70 cc of isopropyl alcohol. After 4 hours, it is noticed an oxygen absorption of 0.03 mole; 0.046 mole of 2-hexanone is formed and 0.064 mole of 1-hexene is consumed (molar selectivity: 57%).

EXAMPLES 2 TO 13

The following examples show that various bimetallic systems may be used to oxidize 1-hexene to 2-hexanone. The operation is as in example 1. Temperature: 40° C, total volume: 100 cc, 1-hexene: 0.236 mole, $O_2$ pressure: 1.2 bars, reaction time: 4 hours.

The following table illustrates these examples.

| EXAMPLE | COMPLEX A 2 millimoles | COMPLEX B 4 m. moles | $O_2$ absorbed m. moles | 1-Hexene consumed (m. moles) | 2-Hexanone formed (m. moles) | MOLAR Selectivity % |
|---|---|---|---|---|---|---|
| 2 | $RhCl_3, 3H_2O$ | $Cu(NO_3)_2, 6H_2O$ | 55 | 115 | 108 | 94 |
| 3 | $RhCl_3, 3H_2O$ | $CuCl_2, 2H_2O$ | 16 | 40 | 36 | 90 |
| 4 | $RhCl_3, 3H_2O$ | $CuF_2$ | 36 | 100 | 78 | 78 |
| 5 | $RhCl_3, 3H_2O$ | $Fe(ClO_4)_2, 6H_2O$ | 42 | 90 | 71 | 79 |
| 6 | $RhCl_3, 3H_2O$ | $FeCl_3$ | 25 | 50 | 36 | 72 |
| 7 | $RhCl_3, 3H_2O$ | $Co(ClO_4)_2, 6H_2O$ | 15 | 35 | 28 | 80 |
| 8 | $RhCl_3, 3H_2O$ | $Ni(ClO_4)_2, 6H_2O$ | 18 | 42 | 30 | 71 |
| 9 | $Rh(NO_3)_3, 2H_2O$ | $CuCl_2, 2H_2O$ | 56 | 125 | 115 | 92 |
| 10 | $[RhCl(C_2H_4)_2]_2$ | $CuCl_2, 2H_2O$ | 47 | 110 | 92 | 84 |
| 11 | $[RhCl(C_8H_{12})]_2$ | $CuCl_2, 2H_2O$ | 50 | 115 | 98 | 85 |
| 12 | $RhCl_3, 3H_2O$ | $Cu(ClO_4)_2 (HMPT)_4$ | 55 | 115 | 108 | 94 |
| 13 | $RhCl_3, 3H_2O$ | $Cu(NO_3)_2 (HMPT)_4$ | 60 | 125 | 115 | 92 |

EXAMPLES 14 – 20

The following examples illustrate the effect of the solvent on the oxidation of 1-hexene to 2-hexanone. The opetion is as described in example 1. Temperature: 41° C, total volume: 100 cc, 1-hexene: 0.236 mole, $O_2$ pressure: 1.2 bars, reaction time: 4 h. The solvents were all anhydrous. The pH of the solutions was roughly 7.

Catalytic system:
[A] : $RhCl_3, 3H_2O$ = 2 m. moles
[B] : $Cu(ClO_4)_2, 6H_2O$ = 4 m. moles The following table illustrates these examples.

| Ex. | Solvent | $O_2$ Absorbed M. Moles | 1-Hexene Consumed m. Moles | 2-Hexanone Formed m. Moles | Molar Selectivity % |
|---|---|---|---|---|---|
| 14 | Methanol | 33 | 51 | 38 | 75 |
| 15 | Ethanol | 58 | 120 | 106 | 88 |
| 16 | Isopropanol | 50 | 109 | 99 | 91 |

-continued

| Ex. | Solvent | O₂ Absorbed M. Moles | 1-Hexene Consumed m. Moles | 2-Hexanone Formed m. Moles | Molar Selectivity % |
|---|---|---|---|---|---|
| 17 | 2-octanol | 28 | 55 | 50 | 91 |
| 18 | Acetone | 11 | 35 | 20 | 57 |
| 19 | CH₃OCH₂CH₂OH | 38 | 75 | 70 | 93 |
| 20 | Propyl ether | 13 | 39 | 24 | 62 |

EXAMPLES 21 – 28

The following examples show that the catalytic systems described therein may be used to oxidize terminal olefins to the corresponding methylketones, while the substituted olefins are not substantially oxidized (2-hexene and 2-octene). The operation is as in example 1, except for examples 21 and 22 wherein the reaction is carried out under pressure in an autoclave.

Temperature: 40° C, reaction volume: 100 cc, reaction time: 4 h.

Catalytic system:
[A] = Rh Cl₃, 3H₂O : 2 m. moles
[B] = Cu (ClO₄)₂, 6H₂O : 4 m. moles.

| Ex. | Olefin 0.236 mole | O₂ Absorbed m. moles | Ketone Formed m. moles | Molar Selectivity % |
|---|---|---|---|---|
| 21 | propylene | 60 | Acetone 115 | 95 |
| 22 | 1-butene | 58 | 2-butanone 110 | 94 |
| 23 | 1-hexene | 50 | 2-hexanone 99 | 91 |
| 24 | 1-octene | 50 | 2-octanone 96 | 86 |
| 25 | 1-decene | 41 | 2-decanone 70 | 87 |
| 26 | styrene | 45 | acetophenone 89 | 85 |
| 27 | 2-hexene | 5 | — | — |
| 28 | 2-octene | 4 | — | — |

EXAMPLES 29 AND 30

These examples are given for comparison of the rhodium based systems and the palladium based systems (not within the scope of the invention), in the oxidation of 1-hexene.

EXAMPLE 29

70 cc anhydrous isopropanol, 2 millimoles rhodium chloride, 4 millimoles Cu (ClO₄)₂(HMPT)₄ complex and 40 millimoles 2,2'-dimethoxypropane for maintaining anhydrous conditions in the medium are introduced into a heat-insulated reactor at 40° C. After 1 hour stirring, 0.236 mole of 1-hexene is added. The pH is about 7. After 4 hours, 70 m. moles oxygen is absorbed; 0.14 mole 2-hexanone is formed and 0.145 mole 1-hexene consumed (selectivity: 96%).

EXAMPLE 30

Example 29 is repeated, except that palladium chloride is used, instead of rhodium chloride. After 4 h, no oxygen has been absorbed and no 2-hexanone is formed.

EXAMPLE 31

This example shows that the palladium systems are active when they are used in a medium containing water, although they are considerably less selective and active than the rhodium systems used in the absence of water, when employed in the oxidation of α-olefins to methyl ketones.

The operating conditions are substantially those of example 29: 0.236 mole of 1-hexene (30 cc), 65 cc of anhydrous isopropanol, 2 millimoles of palladium chloride, 4 millimoles of Cu (ClO₄)₂ (HMPT)₄ complex and 5 cc water are introduced into a heat-insulated reactor and stirred at 40° C at a pH of about 7. After 4 hours of reaction, 25 millimoles of oxygen is absorbed; 25 millimoles of 2-hexanone (selectivity: 41%) and 12 millimoles of 3-hexanone (selectivity: 20%) is formed; 60 millimoles of 1-hexene is consumed. Thus, not only the activity is low but it is found that a mixture of two ketones is formed, instead of only 2-hexanone as in example 29.

What we claim:

1. In a liquid phase process for producing carbonyl compounds by oxidation with molecular oxygen of olefins of the formula $CH_2 = CH - R_2$ containing 3–16 carbon atoms per molecule wherein $R_2$ is an alkyl, aryl, alkylaryl or aralkyl, which process is performed in the presence of a catalytic system comprising both at least one compound (A) of the formula $M_1 X_n L_m$, and at least one compound (B) of the formula $M_2 Z_p L'_q$, X is an anionic group being a halogen, a carboxylate, a sulfate, a nitrate, a perchlorate, a thiocyanate, a tetrafluoroborate, an acetylacetonate or a cyclopentadienyl, Z is an anionic group being a halogen, a carboxylate, a sulfate, a nitrate, a perchlorate or a tetrafluoroborate, $n$, $m$ and $p$ are integers selected from 1, 2 and 3, $M_2$ is a metal being iron, cobalt, nickel or copper, $q$ is zero or an integer from 1 to 6, inclusive, L is a coordinate being $H_2O$, a mono-olefin, a poly-olefin, a phosphine, dimethylsulfoxide or acetylacetonate, and L' is a coordinate being $H_2O$, dimethylformamide, hexamethylphosphoramide or dimethylsulfoxide,
    wherein the improvement comprises conducting the said process under maintained anhydrous conditions in an anhydrous organic solvent selected from the group consisting of methanol, ethanol, n-propanol, isopropanol, 2-butanol, 3,3-dimethyl-2-butanol, 2-octanol, cyclohexanol, methyl phenyl carbinol, ethylene glycol, 1,2-propane diol, glycerol and glycol monomethyl ether, and wherein $M_1$ is rhodium.

2. A process according to claim 1, wherein the pH of the reaction medium is substantially from 6 to 8.

3. A process according to claim 1, wherein (A) is a compound of the formulae Rh F₃, 3H₂O; Rh Cl₃, 3H₂O; Rh Br₃, 2H₂O;
    [Rh X (mono-olefin)₂]₂ or [Rh X (polyolefin)]₂ where the olefin is ethylene or propylene, and the polyolefin is selected from cyclooctadiene, butadiene, cyclohexadiene and cyclododecatriene, and wherein (B) is:
    a perchlorate or nitrate of the formulae: M₂(ClO₄)₂, 6 H₂O and M₂ (NO₃)₂, 6 H₂O,
    a copper or iron halide of the formula $M_2Z_p$, qH₂O where Z is fluorine, chlorine or bromine, M₂ is iron or copper, $p$ is 2 or 3, and $q$ is 0 or an integer from 1 to 6,
    or a complex of the formulae Cu (ClO₄)₂, 4 L'; Fe (ClO₄)₂, 4 L' or Cu (NO₃)₂, 4 L' where L' is a coordinate being dimethylformamide, hexamethyl phosphoramide or dimethylsulfoxide.

4. A process according to claim 1, wherein the organic solvent is isopropanol, methyl cellosolve (glycol monomethylether) or 2-octanol.

5. A process according to claim 4, wherein the catalytic system consists essentially of hydrated rhodium chloride and copper perchlorate of the formula $Cu(ClO_4)_2, 6H_2O$.

6. A process according to claim 4, wherein the catalytic system comprises both: (1) a compound of the formulae $Rh Cl_3, 3H_2O$; $Rh(NO_3)_3, 2 H_2O$ or $Rh Br_3, 3 H_2O$, and (2) a compound of the formulae $Cu(NO_3)_2, 6 H_2O$; $Cu Cl_2, 2 H_2O$; $Cu F_2$; $Fe(ClO_4)_2, 6 H_2O$; $Fe Cl_3$; $Co(ClO_4)_2, 6H_2O$; $Ni(ClO_4)_2, 6 H_2O$; $Cu(ClO_4)_2 (HMPT)_4$ or $Cu(NO_3)_2 (HMPT)_4$.

7. A process according to claim 1 wherein the temperature of the oxidation reaction is from 0° to 150° C.

8. A process according to claim 1, wherein the reaction medium contains 2,2'-dimethoxypropane as a dehydration agent.

9. A process according to claim 1, wherein one of L and L' is other than $H_2O$.

10. A process according to claim 1, wherein one of L and L' is other than $H_2O$.

* * * * *